United States Patent
Henderson (10) Patent No.: US 6,492,349 B1
(45) Date of Patent: *Dec. 10, 2002

(54) AMINOSUGAR AND GLYCOSAMINOGLYCAN COMPOSITION FOR THE TREATMENT AND REPAIR OF CONNECTIVE TISSUE

(75) Inventor: Robert W. Henderson, Baldwin, MD (US)

(73) Assignee: Nutramax Laboratories, Inc., Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 375 days.

(21) Appl. No.: 08/779,996

(22) Filed: Dec. 23, 1996

Related U.S. Application Data (63) Continuation-in-part of application No. 08/207,581, filed on Mar. 14, 1994, now Pat. No. 5,587,363, which is a continuation-in-part of application No. 08/040,936, filed on Mar. 31, 1993, now Pat. No. 5,364,845.

(51) Int. Cl.[7] .................. A61K 31/715; A61K 31/70; C07H 1/00
(52) U.S. Cl. .................. 514/54; 514/53; 514/62; 536/55.2; 536/123; 536/123.1; 536/123.13
(58) Field of Search .................. 514/54, 53, 62; 536/55.2, 123.1, 123, 123.13

(56) References Cited

U.S. PATENT DOCUMENTS

| | | | |
|---|---|---|---|
| 3,232,836 A | 2/1966 | Carlozzi et al. | 167/65 |
| 3,371,012 A | 2/1968 | Furuhashi | 167/59 |
| 3,683,076 A | 8/1972 | Rovati | 424/180 |
| 3,697,652 A | 10/1972 | Rovati et al. | 424/180 |
| 4,006,224 A | 2/1977 | Prudden | 424/180 |
| 4,473,551 A | 9/1984 | Schinitsky | 424/95 |
| 4,486,416 A | 12/1984 | Soll et al. | 424/180 |
| 4,801,619 A | 1/1989 | Lindblad | 514/825 |
| 4,983,580 A | 1/1991 | Gibson | 514/2 |
| 5,141,928 A | 8/1992 | Goldman | 514/54 |
| 5,364,845 A | * 11/1994 | Henderson | 514/54 |
| 5,587,363 A | * 12/1996 | Henderson | 514/54 |
| 5,721,361 A | * 2/1998 | Lennon | 540/450 |

FOREIGN PATENT DOCUMENTS

FR    2609397    7/1988    ......... A61K/31/70

OTHER PUBLICATIONS

"Vetrazene" Literature, Vetraceutical Services, Inc., 1996.
Calia, Kurt Geoffrey; Cover Letter to USPTO with Jan. 11, 1996, data stamp indicating receipt of Petition to Make Special and the documentation in support of that petition; pp. 1–2.
Calia, Kurt Geoffrey; Petition to Make Special; Jan. 11, 1996; pp. 1–2.

(List continued on next page.)

Primary Examiner—Gary Geist
Assistant Examiner—Everett White
(74) Attorney, Agent, or Firm—Covington & Burling; Paul J. Berman (57) ABSTRACT

A therapeutic composition for the protection, treatment and repair of connective tissue in mammals and a method for the treatment of connective tissue in mammals by the administration of the composition. The composition includes glucosamine and preferably chondroitin sulfate or fragments thereof. The composition optionally includes manganese ascorbate which catalyzes the production of collagen and proteoglycans from the glucosamine and chondroitin sulfate.

23 Claims, 3 Drawing Sheets

OTHER PUBLICATIONS

Henderson, Robert J.; Declaration by Applicant in Support of Petition to Make Special; Jan. 2, 1996; pp. 1–5, Exhibits A, B, C, and D.

Calia, Kurt Geoffrey; Declaration by Attorney in Support of Pettition to Make Special; Jan. 11, 1996; pp. 1–3.

Morrison et al, "Coronary Heart Disease and the Mucopolysaccharides (Glycosaminoglycans)," C.C. Thomas, Publisher, pp. 12–13; 109–127 (1973).

Drovanti et al, "Therapeutic Activity of Oral Glucosamine Sulfate in Osteoarthrosis; A Placebo–Controlled Double–Blind Investigation," Clin. Therap., 3(4) 260–272 (1980).

Karzel et al, "Effects of Hexosamine Derivatives and Uronic Acid Derivatives on Glycosaminoglycane Metabolism of Fibroblast Cultures," Pharmacology 5: 337–345 (1971).

Setnikar et al, "Pharmacokinetics of Glucosamine in the Dog and in Man," Arzneim. –Forsch., 36 (I) 729–735 (1986).

Vidal y Plana et al, "Articular Cartilage Pharmacology: I. In Vitro Studies on Glucosamine and Non–Steroidal Anti–inflammatory Drugs," Pharm. Res. Comm., 10 (6) 557–569 (1978).

Anon., "Using a Chondroprotective Drug in Treating Dogs With Osteochondrosis," Veterinary Medicine, 130 (Feb. 1993).

Bucci, "Manganese: Its Role in Nutritional Balance," Today's Chirop., 17(2) 23–28, 44 (1988).

Bucci, "Glucosamine—A New Potent Nutraceutical For Connective Tissues," The Nutritional Supplement Advisor (Jul. 1992).

Banks, "Applied Veterinary Histology," Williams and Wilkins Publisher, pp. 84–85 (1986).

"Current Therapy in Equine Medicine 2," Robinson, Editor, W.B. Saunders Co., Publisher, pp. 402–403 (1987).

Garrison, Jr., et al, "The Nutrition Desk Reference," Keats Publishing, Inc., pp. 70–71 (1985).

Christensen, "Nutritional Support For Injury Rehabilitation Specific Needs For The Three Phases of Rehabilitation, " Chiropractic Products, pp. 100–102 (Apr. 1993).

Murray, "A Natural Treatment of Osteoarthritis," MPI's Dyanmic Chiropratic, pp. 8–10, Sep. 12, 1993.

Bucci, "Chondroproductive Agents Glucosamine Salts and Chrondroitin Sulfates," Townsend Letters for Doctors, pp. 52–54, Jan. 1994.

Hardingham et al, "Proteoglycans: Many Forms and Many Functions," 6 FASEB J. 861, 862 (1992).

Champe et al, Lippincott's Illustrated Reviews: Biochimistry, pp. 148–150 (2nd ed. 1994).

Szabo et al, "Sulfhydryl Compounds May Mediate Gastric Cytoprotection," Science, 214: 200–202 (Oct. 1981).

Conroy et al, "Occurrence of Ornithine Decarboxylase and Polyamines in Cartilage," Biochem. J., 162: 347–350 (1977).

Bucci, "Nutrition Applied to Injury Rehabilitation and Sports Medicine," CRC Press, Inc. (1994).

* cited by examiner

AMINOSUGAR AND GLYCOSAMINOGLYCAN COMPOSITION FOR THE TREATMENT AND REPAIR OF CONNECTIVE TISSUE

CROSS REFERENCE TO RELATED APPLICATION

This application is a continuation-in-part of application Ser. No. 08/207,581 filed on Mar. 14, 1994, now U.S. Pat. No. 5,587,363, which is a continuation-in-part of application Ser. No. 08/040,936 filed on Mar. 31, 1993, now U.S. Pat. No. 5,364,845. The disclosure of U.S. Pat. No. 5,587,363 is incorporated by reference herein in its entirety.

BACKGROUND OF THE INVENTION

1. Field of the Invention

The present invention relates to therapeutic compositions for the repair of connective tissue in humans and animals and, in particular to nutraceutical compositions capable of promoting chondroprotection, the repair and replacement of human and animal connective tissue.

2. Background

The connective tissues of humans and animals are constantly subjected to stresses and strains from mechanical forces that can result in afflictions, such as arthritis, joint inflammation and stiffness. Such afflictions are especially acute in joints, such as the neck, back, arms, hips, ankles and feet. Indeed, connective tissue afflictions are quite common, presently affecting millions of Americans. Further, such afflictions can be both painful and, in their extreme, debilitating.

The treatment of connective tissue afflictions can be quite problematic. A simple decrease in the stress to which the connective tissue is subjected is often not usually an option, especially in the case of athletes and animals such as race horses. Thus, an interruption in the traumatic pathways can often not be achieved. Consequently, especially in the case of human athletes and animals, treatment is often directed at controlling the symptoms of the afflictions and not their causes, regardless of the stage of the degenerative process.

Presently, steroids, such as corticosteroids, and other anti-inflammatory materials, such an NSAIDS or high doses of aspirin, are widely used for the treatment of connective tissue ailments. [Vidal et al., *Pharmocol. Res. Commun.,* 10:557–569 (1978)]. In addition, hyaluronic acid and polysulfated glycosaminoglycan are used in veterinary medicine, especially for equines. Drugs may inhibit the body's own natural healing processes, leading to further deterioration of the connective tissue.

Connective tissues are naturally equipped to repair themselves by manufacturing and remodeling prodigious amounts of collagen (a chief component of connective tissues) and proteoglycans (PGs)—the other major component of connective tissues. This ongoing process is placed under stress when an injury occurs to connective tissues. In such cases, the production of connective tissue (along with collagen and proteoglycans) can double or triple over normal amounts, thereby increasing the demand for the building blocks of both collagens and proteoglycans.

The building blocks for collagen are amino acids, especially proline, glycine and lysine. Proteoglycans (PGs) are large and complex macromolecules comprised mainly of long chains of modified sugars called glycosaminoglycans (GAGS) or mucopolysaccharides. PGs provide the framework for collagen formation and also hold water to give the connective tissues (especially cartilage) flexibility, resiliency and resistance to compression.

Like almost every biosynthetic pathway in the body, the pathways by which both collagen and GAG form single molecule precursors are quite long. As is also characteristic of other biosynthetic pathways, the pathways by which collagen and GAGs are produced include what is called a rate-limiting step—that is, one highly regulated control point beyond which there is a commitment to finish. The presence of such rate-limiting steps permits complicated biosynthetic processes to be more easily and efficiently controlled by permitting the organism to focus on one point. For example, if conditions demand production and all the requisite raw materials are in place, then stimulation of the rate-limiting step will cause the end product to be produced. To stop or slow production, the organism needs simply to regulate the rate-limiting step.

In the production of collagen, the rate-limiting step is the maturation, rather than the production, of newly synthesized collagen. Unused collagen in simply degraded back to amino acids. Proteoglycans, however, have a specific rate-limiting step in their production.

In the production of PGs, the rate-limiting step is the conversion of glucose to glucosamine for the production of GAGs. Glucosamine, an aminosugar, is the key precursor to all the various modified sugars found in GAGs, including glucosamine sulfate, galactosamine, N-acetylglucosamine, etc. Glucosamine also makes up to 50% of hyaluronic acid—the backbone of PGs—on which other GAGs, like chondroitin sulfate are added. The GAGs are then used to build PGs and, eventually, connective tissue. Once glucosamine is formed, there is no turning away from the synthesis of GAG polymers and the synthesis of collagen.

Glucosamine has been shown to be rapidly and almost completely absorbed into humans and animals after oral administration. A significant portion of the ingested glucosamine localizes to cartilage and joint tissues, where it remains for long periods. This indicates that oral administration of glucosamine reaches connective tissues, where glucosamine is incorporated into newly-synthesized connective tissue. In vitro, the introduction of glucosamine has been demonstrated to increase the synthesis of collagen and glycosaminoglycans in fibroblasts, which is the first step in repair of connective tissues. In vivo, topical application of glucosamine has enhanced wound healing. Glucosamine has also exhibited reproducible improvement in symptoms and cartilage integrity in humans with osteoarthritis in a series of studies. [L. Bucci, *Nutritional Supplement Advisor,* (July 1992)].

The pathway for the production of connective tissue may be briefly described as follows. Glucosamine is the main building block of connective tissue and may be provided either through the enzymatic conversion of glucose or through diet or external administration (see FIG. 1). Glucosamine may be converted into the other main component of connective tissue, namely proteoglycans (PGs), upon incorporation of glucosamine into glycosaminoglycans (GAGs) (see FIG. 2).

More specifically, GAGs are large complexes of polysaccharide chains associated with a small amount of protein. These compounds have the ability to bind large amounts of water, thereby producing a gel-like matrix that forms the body's ground substance. GAGs stabilize and support cellular and fibrous components of tissue while maintaining the water and salt balance of the body. The combination of insoluble protein and the ground substance forms connective tissue. For example, cartilage is rich in ground substance while tendon is composed primarily of fibers.

GAGs are long chains composed of repeating disaccharide units of monosaccharides (aminosugar-acidic sugar repeating units). The aminosugar is typically glucosamine or galactosamine. The aminosugar may also be sulfated. The acidic sugar may be D-glucaronic acid or L-iduronic acid. GAGs, with the exception of hyaluronic acid, are covalently bound to a protein, forming proteoglycan monomers. These PGs consist of a core protein to which linear carbohydrate chains formed of monosaccharides are attached. In cartilage proteoglycan, the species of GAGs include chondroitin sulfate and keratin sulfate. The proteoglycan monomers then associate with a molecule of hyaluronic acid to form PG aggregates. The association of the core protein to hyaluronic acid is stabilized by link proteins.

The polysaccharide chains are elongated by the sequential addition of acidic sugars and aminosugars, and the addition is catalyzed by a family of transferases. Aminosugars, such as glucosamine, are synthesized through a series of enzymatic reactions that convert glucose to glucosamine, or alternatively may be provided through the diet. The glucosamine is then incorporated into the GAGs as described above. Acidic sugars may be provided through the diet, may be obtained through degradation of GAGs by degradative enzymes, or produced through the uronic acid pathway.

Figure 1:
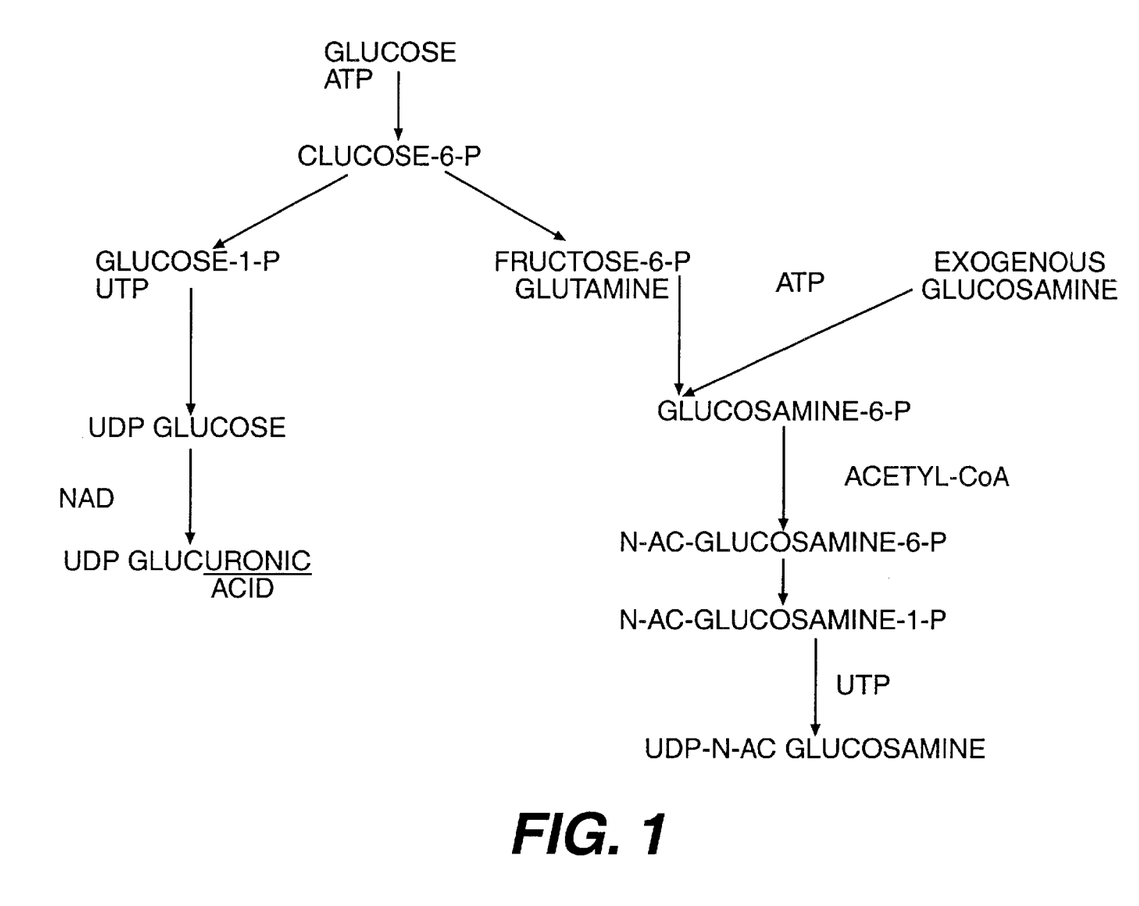
FIG. 1 is a sequence for the biosynthesis of hexosamines, including glucosamine.

Since repeating disaccharide units contain one aminosugar (such as glucosamine), it is clear that the presence of an aminosugar in the production of connective tissue is important. Glucosamine is, by far, the more important ingredient in the production of connective tissue since it is the essential building block of GAGs. See FIG. 1. The glucosamine is provided from the composition of the present invention. All GAGs contain hexosamine or uronic acid derivative products of the glucose pathway and from exogenous glucosamine for example:

| Hyaluronic acid | Glucosamine + Glucaronic Acid |
| Keretan-Sulfate | Glucosamine + Galactose |
| Chondroitin Sulfate | Glucaronic Acid + Galactosamine |
| Heparin Sulfate | Glucosamine + Glucaronic or Iduronic Acid |
| Heparan Sulfate | Glucosamine + Glucaronic or Iduronic Acid |
| Dermatin Sulfate | Iduronic Acid + Galactosamine |

Chondroitin sulfate is a GAG that provides a further substrate for the synthesis of the proteoglycans. The provision of the chondroitin in its salt (sulfate) form facilitates its delivery and uptake by the humans and animals in the production of connective tissue. In addition, the sulfate portion of chondroitin sulfate is available for use in catalyzing the conversion of glucosamine to GAGs. Fragments of GAGs, including chondroitin sulfate, may also be used to provide a substrate for synthesis of proteoglycans since the assembly of PG occurs in the extracellular space.

In addition, chondroitin sulfate has been shown to have cardiovascular health benefits. [Morrison et al., *Coronary Heart Disease and the Mucopolysaccharides (Glycosaminoglycans)*, pp. 109–127 (1973)]. Thus, the preferred form of glycosaminoglycan included in the compositions of the present invention is chondroitin sulfate or fragments thereof.

Chondroitin may be more efficacious than glucosamine for injury rehabilitation. [Christensen, *Chiropractic Products*, pp. 100–102 (April 1993)]. An evaluation of glucosamine versus chondroitin for treatment of osteoarthritis has been conducted and concludes, contrary to Christensen, that glucosamine is preferred. [Murray, *MPI's Dynamic Chiropractic*, pp. 8–10 (Sep. 12, 1993)]. Neither reference teaches or suggests combining of the materials. Bucci (*Townsend Letter for Doctors*, pp. 52–54, January 1994), who was aware of the applicant's composition and acknowledges personal communication from the applicant, discloses the combination of glucosamine and chondroitin for treatment of osteoarthritis.

Chondroitin sulfate also acts to inhibit the degradative enzymes that break down connective tissue. In so doing, chondroitin sulfate promotes the maintenance of healthy connective tissues. When combined with glucosamine, which functions primarily as a building block for the synthesis of connective tissue, chondroitin sulfate works in concert with the glucosamine but works in a primarily different fashion. The ability of chondroitin sulfate to block degradation is an important function, and chondroitin sulfate is provided in the compositions of the present invention primarily for that reason.

Manganese, a stimulant to the composition, plays a role in the synthesis of GAGs, collagen and glycoproteins which are important constituents of cartilage and bone. For that reason, manganese is an optional ingredient in the compositions of the present invention. Manganese is important for enzyme activity of glycosyltransferases. This family of enzymes is responsible for linking sugars together into glycosaminoglycans, adding sugars to other glycoproteins, adding sulfate to aminosugars, converting sugars into other modified sugars, and adding sugars to lipids. The enzymatic functions of glycosyltransferases are important in glycosaminoglycan synthesis (hyaluronic acid, chondroitin sulfate, keratan sulfate, heparin sulfate and dermatin sulfate, etc.), collagen synthesis, and in the functions of many other glycoproteins and glycolipids. Glycosaminoglycans and collagen are the chief structural elements of all connective tissues. Their synthesis is essential for proper maintenance and repair of connective tissues.

Manganese deficiency leads to abnormal bone growth, swollen and enlarged joints, and slipped tendons in humans and animals. In humans, manganese deficiencies are also associated with bone loss and arthritis. Levels of all glycosaminoglycans are decreased in connective tissues during manganese deficiencies, with chondroitin sulfates being most depleted. Manganese-deficient organisms quickly normalize glycosaminoglycans and collagen synthesis when manganese is replenished.

Manganese is also important for activity of manganese superoxide dismutase (MnSOD), which is present only in mitochondria. Manganese deficiency decreases the activity of MnSOD and may lead to mitochondrial dysfunction, manifested as decreased cellular functions.

Approximately 40% of dietary manganese is absorbed by the body tissue. Storage of manganese in the body is minimal—a mere 12 to 20 mg is present in the body at any one time. Large amounts of calcium and phosphorus in the intestine are known to interfere with absorption. The richest dietary sources are the foods least consumed by the general public as whole grain cereals and breads, dried peas, beans and nuts. The ascorbate form of manganese is preferred in the present invention due to the high bioavailability and the need for vitamin C (ascorbic acid) for collagen production. Vitamin C also enhances manganese uptake by the body. However, other soluble forms of manganese may be used in the present invention as well.

Manganese also plays a role in the synthesis of glycosaminoglycans and glycoproteins, which are important constituents of cartilage and bone. Many reproductive problems in horses and skeletal abnormalities in foals have been ascribed to manganese deficiency. [*Current Therapy in Equine Medicine*, 2:402–403 (1987)].

3. Description of Prior Art

There are several disclosures of which we are aware wherein it has been suggested to provide exogenous quantities of glucosamine in order to bypass the rate-limiting step of the conversion of glucose to glucosamine in those pathways that produce proteoglycans. For example, the intravenous administration of glucosamine (a precursor of the GAGs) and derivatives thereof have been disclosed in U.S. Pat. No. 3,232,836, issued to Carlozzi et al., for assisting in the healing of wounds on the surface of the body. In U.S. Pat. No. 3,682,076, issued to Rovati, the use of glucosamine and salts thereof is disclosed for the treatment of arthritic conditions. Finally, the use of glucosamine salts has also been disclosed for the treatment of inflammatory diseases of the gastrointestinal tract in U.S. Pat. No. 4,006,224 issued to Prudden.

There have also been several disclosures of which we are aware wherein it has been suggested to go one step further in bypassing the glucose-to-glucosamine rate-limiting step, by providing exogenous quantities of various of the modified sugars found in the GAGs for producing proteoglycans. For example, in U.S. Pat. No. 3,6797,652 issued to Rovati et al., the use of N-acetylglucosamine is disclosed for treating degenerative afflictions of the joints.

In still other disclosures of which we are aware, it has been taught to go still one step further in bypassing the glucose-to-glucosamine rate-limiting step by providing exogenous quantities of the GAGs themselves (with and without various of the modified sugars). For example, in U.S. Pat. No. 3,371,012 issued to Furuhashi, a preservative is disclosed for eye graft material that includes galactose, N-acetylglucosamine (a modified sugar found in the GAGs) and chondroitin sulfate (a GAG). Additionally, U.S. Pat. No. 4,486,416 issued to Soll et al., discloses a method of protecting corneal endothelial cells exposed to the trauma of intraocular lens implantation surgery by administering a prophylactically effective amount of chondroitin sulfate. Also, U.S. Pat. No. 5,141,928 issued to Goldman discloses the prevention and treatment of eye injuries using glycosaminoglycan polysulfates.

U.S. Pat. No. 4,983,580 issued to Gibson, discloses methods for enhancing healing of corneal incisions. These methods include the application of a corneal motor composition of fibronectin, chondroitin sulfate and collagen to the incision.

Finally, in U.S. Pat. No. 4,801,619 issued to Lindblad, the intraarticular administration of hyaluronic acid is disclosed for the treatment of progressive cartilage degeneration caused by proteoglycan degradation.

While the above references have, to varying degrees, been useful for their intended purposes, none has proven entirely satisfactory. In particular, the absorption rates and ability to increase GAG production of the various compositions disclosed in these references have not been entirely satisfactory. In addition, none of the compositions are provided with both the aminosugar starting material in conjunction with a GAG (such as chondroitin sulfate) or fragments of GAGs, including chondroitin sulfate.

Accordingly, it can be seen that there remains a need for a therapeutic composition which includes an aminosugar and GAGs or fragments of GAGs for aiding in the conversion of the building blocks of connective tissue to proteoglycans for facilitating the repair of connective tissue in humans and animals.

SUMMARY OF INVENTION

It is an object of the present invention to provide a therapeutic composition for the protection and repair of connective tissue in humans and animals.

It is a further object of the present invention to provide such a therapeutic composition which is a nutraceutical— that is, a composition which includes only naturally-occurring components capable of providing beneficial therapeutic effects.

It is yet another object of the present invention to provide such a nutraceutical which contains an aminosugar and which further contains glycosaminoglycans for facilitating the repair of connective tissue in humans and animals.

It is still a further object of the present invention to provide such a nutraceutical which contains an aminosugar and which further contains fragments of glycosaminoglycans for facilitating the repair of connective tissue in humans and animals.

It is a further object of the present invention to provide such a nutraceutical composition which exhibits increased absorption rates.

In accordance with the present invention, disclosed herein is a composition capable of treating and repairing connective tissue in humans and animals. The composition includes therapeutic quantities of an aminosugar selected from the group consisting of glucosamine, glucosamine salts and mixtures thereof, in combination with a glycosaminoglycan selected from the group consisting of chondroitin, chondroitin salts and mixtures thereof, and fragments of a glycosaminoglycan selected from the group consisting of fragments of chondroitin, fragments chondroitin salts and mixtures of such fragments.

In further accordance with the teachings of the present invention, disclosed herein is a method for the treatment and repair of connective tissue in humans and animals. This method includes administering a therapeutically effective quantity of a therapeutic composition including an aminosugar selected from the group consisting of glucosamine, glucosamine salts and mixtures thereof, in combination with a glycosaminoglycan selected from the group consisting of chondroitin, chondroitin salts and mixtures thereof, and fragments of a glycosaminoglycan selected from the group consisting of fragments of chondroitin, fragments of chondroitin salts and mixtures of such fragments.

These and other objects of the present invention will become readily apparent from a reading of the following description, when taken in conjunction with the enclosed drawing.

DETAILED DESCRIPTION OF THE INVENTION

DESCRIPTION OF PREFERRED EMBODIMENTS

The composition of the present invention includes an aminosugar, such as glucosamine (preferably in a salt form)

and a glycosaminoglycan, such as chondroitin (preferably in a salt form as the sulfate). Alternatively, fragments of a glycosaminoglycan may be used in the compositions of the invention. According to the principles of the present invention, a composition of glucosamine and chondroitin (or fragments thereof) is provided to humans and animals in need thereof. Manganese salts such as manganese ascorbate may be added because the ascorbate is a soluble salt which also provides ascorbic acid needed for collagen synthesis. When provided in such fashion, the manganese functions as a cofactor, a substance that aids the aminosugar and glycosaminoglycan in the production of connective tissue. Other manganese salts such as sulfate or gluconate may be used. In this fashion, the glucose-to-glucosamine rate-limiting step in the human's or the animal's natural production of collagen and proteoglycans will be bypassed, for production of additional quantities of collagen and proteoglycans, so as to be available for use by the human's or the animal's natural healing processes to repair connective tissue.

The aminosugar glucosamine is the base of the composition, providing the primary substrate for both collagen and proteoglycan synthesis. In fact, glucosamine is the preferred substrate for proteoglycan synthesis, including chondroitin sulfates and hyaluronic acid. The glucosamine preferably is in a salt form so as to facilitate its delivery and uptake by humans and animals. The preferred salt forms are glucosamine hydrochloride, glucosamine sulfate and N-acetylglucosamine.

In the present method for the treatment and repair of connective tissue in humans and animals, therapeutic amounts of exogenous quantities of glucosamine including salts thereof in combination with chondroitin sulfate, are administered to humans and animals in need thereof for stimulating both collagen and proteoglycan synthesis. Manganese salts are also provided in those cases where there is a deficiency of manganese. In other words, manganese is an optional component in the compositions of the present invention.

In the present method for the treatment and repair of connective tissue in humans and animals, therapeutic amounts of exogenous quantities of glucosamine including salts thereof in combination with fragments of chondroitin sulfate, are administered to humans and animals in need thereof for stimulating both collagen and proteoglycan synthesis.

Figure 2:
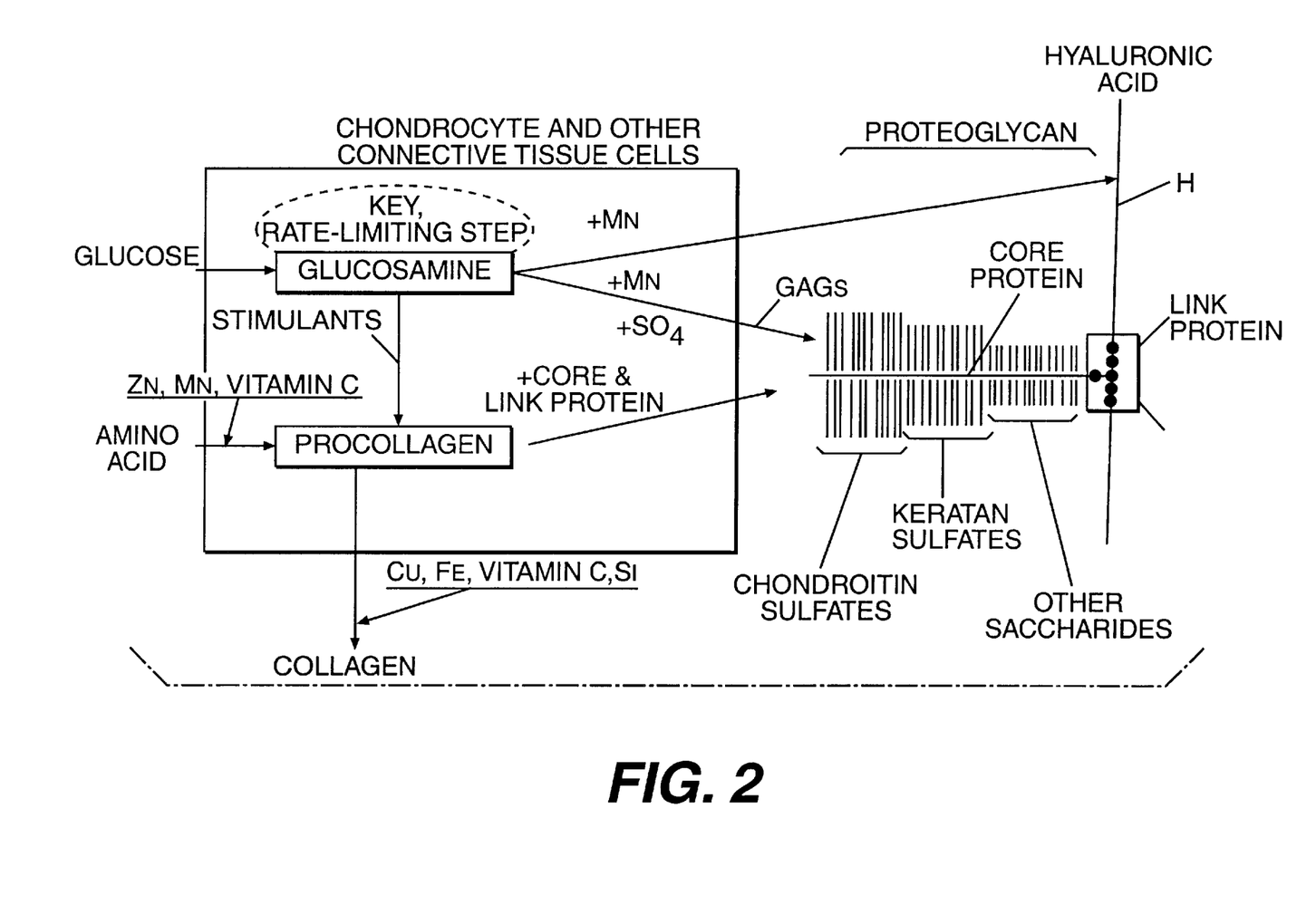
FIG. 2 is a schematic flowchart illustrating the biological pathway by which the composition of the present invention aids in the protection and repair of connective tissue.
Figure 3:
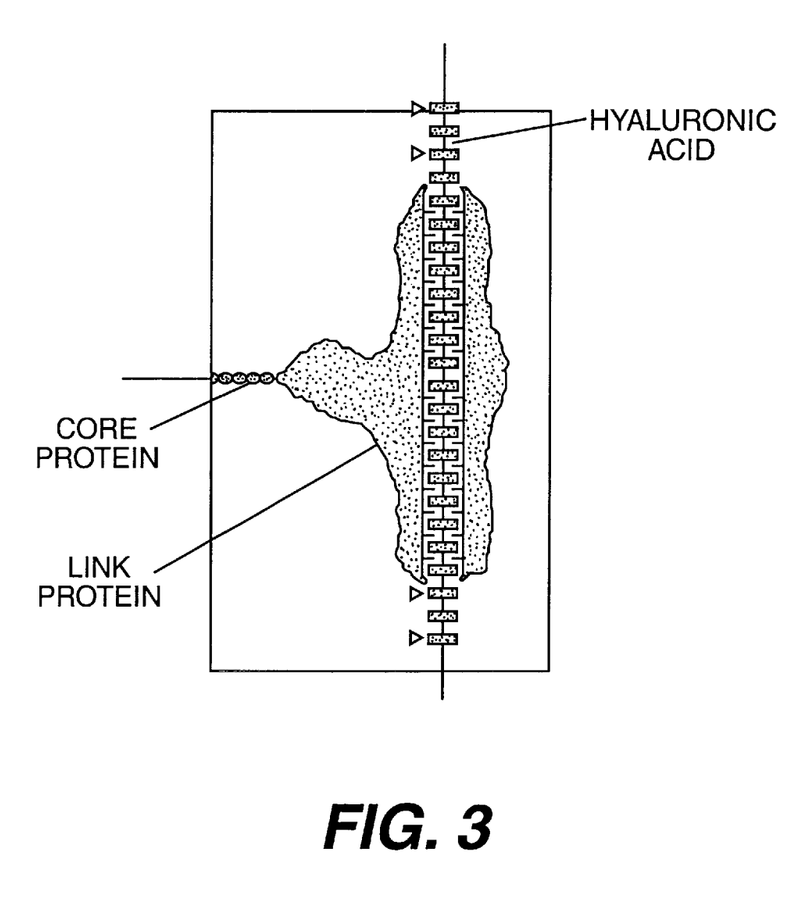
FIG. 3 is an enlarged portion of the flowchart of FIG. 2.

Referring to FIGS. 2 and 3, the biosynthetic pathway for the production of connective tissue, which is affected by the method of the present invention by virtue of the components of the composition of the present invention which aid in connective tissue repair, functions as described in the above background section.

Administration of the composition of the present invention provides the human or animal organism with exogenous quantities of the aminosugar and glycosaminoglycan or fragments thereof. If required, the composition also provides the human or animal organism with exogenous quantities of manganese cofactors.

The composition of the present invention has been satisfactorily used in the treatment and repair of connective tissue in a broad spectrum of humans and animals which have joints subject to stress and strain. Mammals, including humans, dogs, cats, pigs, horses and cattle have been treated. Also, avian species showing arthritic type conditions have responded favorably to treatment. Parrots, penguins and ratites have been treated.

The exogenous glucosamine provided by the composition of present invention is converted to both proteoglycans and collagen, as is seen in FIG. 2 and as described above.

In the former case, the glucosamine may be converted with the aid of manganese directly into GAG, including hyaluronic acid (which is 50% glucosamine and which forms the backbone of the proteoglycans). Manganese cofactors are usually present in sufficient quantities in the human or animal being treated. In the event that there a deficiency of manganese cofactors exists, however, a soluble manganese salt may optionally be included in the composition of the present invention. This core protein is then linked to the hyaluronic acid via the link protein, as is seen in FIG. 3.

The free amino acids are, with the aid of the manganese and zinc cofactors (and ascorbic acid or vitamin C), converted to procollagen. The procollagen is then converted into collagen with the aid of copper or iron cofactors and vitamin C (ascorbic acid) and sulfate chelates.

The efficacy of the composition of the present invention has been demonstrated. In vitro cultures of cartilage and connective tissue cells that were provided with the composition of the present invention produced more hyaluronic acid, more chondroitin sulfate, more collagen and more matrix than controls or other GAG precursors. While glucosamine increased GAG production by 170% in cultured connective tissue calls, other modified sugars or GAG components were ineffective.

Furthermore, administration of the glucosamine in the composition of the present invention to human and animal cartilage explants improved biomechanical properties. Physiological (low) doses increased cartilage synthesis in humans and animals by 10% which is quite large in real life.

Glucosamine is naturally-occurring in connecting tissue and can be considered a nutrient when ingested in foods. Although usually a part of connective tissue, glucosamine is a normal body component that happens to be an important control element and raw material.

Furthermore, since glucosamine is a small, naturally-occurring molecule, it is almost completely absorbed (greater than 95%) when given orally, as shown by human and animal studies. Even more important, 30% of an oral dose is retained by the musculoskeletal system for long time periods. Daily oral dosing was found to raise tissue levels of glucosamine better than intravenous administration. Glucosamine is non-toxic, with oral doses of 8 grams per Kg body weight to mice, rats, rabbits and dogs not causing any problems, even after months of dosing. [L. Bucci, *The Nutritional Supplement Advisor* (July 1992)].

Thus, it can be seen that the composition of the present invention containing glucosamine and purified chondroitin sulfates and mixtures and fragments thereof, advantageously stimulates the synthesis of collagen and glycosaminoglycans or mucopolysaccharides (GAGs), including hyaluronic acid, the backbone of proteoglycans (PGs), thereby providing a natural tissue repair function. This composition provides the superior connective tissue repair function of glucosamine, plus the above-described benefits from chondroitin sulfates and fragments of chondroitin sulfates. Manganese provides a further benefit if a deficiency of the mineral exists. The tissue repair can be in the context of cartilage repair and the treatment of arthritic conditions as well as connective tissue damage in most all areas of the body both human and animal.

Having discussed the composition of the present invention, it will be more clearly perceived and better understood from the following specific examples.

The composition of the present invention is made in a capsule form for oral administration to humans and small animals in need thereof. Each capsule contains:

| Human & Small Animal | Tabs, Capsules | Range/Dose |
|---|---|---|
| Glucosamine | 250 mg | 100–2500 mg |
| Chondroitin Sulfate | 200 mg | 15–500 mg |

For those situations in which a manganese deficiency exists, a manganese salt is added so that each capsule contains:

| Human & Small Animal | Tabs, Capsules | Range/Dose |
|---|---|---|
| Glucasamine | 250 mg | 100–500 mg |
| Chondroitin Sulfate | 200 mg | 15–500 mg |
| Manganese (as Ascorbate) | 5 mg | 2–25 mg |
| Ascorbate (as Manganese Ascorbate) | 33 mg | 13–165 mg |

Dosages of 1–6 capsules or scoops as appropriate (or more as otherwise needed) are administered daily to the human and animal in need thereof to effectuate connective tissue protection and repair.

For larger animals—such as horses, the composition is administered as filled scoops.

| Large Animal (Equine) | Level Scoopful | Range/Dose |
|---|---|---|
| Glucosamine | 1800 mg | 500–5000 mg |
| Chondroitin Sulfate | 600 mg | 100–3000 mg |

For those situations in which a manganese deficiency exists, manganese salts may be added so that each capsule contains:

| Large Animal (Equine) | Level Scoopful | Range/Dose |
|---|---|---|
| Glucosamine | 1800 mg | 500–5000 mg |
| Chondroitin Sulfate | 600 mg | 100–3000 mg |
| Nanganese (as Ascorbate) | 16 mg | 10–125 mg |
| Ascorbate (as Manganese Ascorbate) | 104 mg | 65–825 mg |

The composition may omit the manganese salt if desired. Also, the composition may be administered parenterally if desired.

The following case studies were conducted with mammals. The unexpected speed of response of human and animal recovery demonstrate the effectiveness of the treatment. The treatment included manganese salts which were included to insure against manganese deficiencies.

Case #1

Five month old female intact Rottweiler, presented with chief complaint of difficulty getting up in the rear and occasional crying in pain when walking. Physical exam revealed pain on palpation of hips with crepitation in right hip. Preliminary diagnosis was hip dysplasia. Radiographs diagnosed bilateral hip dysplasia with approximately ¼ of femoral head seated in the acetabulum. The owners were contemplating euthanasia. The dog was placed on three (3) capsules of the present invention two times daily for two weeks. At two week recheck, the dog was moving better and getting up easier. At one month, the dog was running, climbing stairs, and the owners were surprised. The animal is presently doing well and is still on a maintenance dose of two (2) capsules two times daily.

Case #2

A nine year old intact pure bread certified Rottweiler presented with difficulty rising in rear and a wobbly gait in the hind quarters. Physical exam revealed pain on manipulation of hips. A preliminary diagnosis of degenerated joint disease (DJD) was made. The dog was placed on three (3) capsules of the present invention two times daily for one month and re-evaluated at two weeks and one month. At two weeks, the dog was rising better, and the gait was almost normal at one month. The dog was 65% improved according to the breeder and improving weekly. The dog is currently on a maintenance dose of two (2) capsules two times daily.

Case #3

A 12 year old neutered Collie presented with generalized muscle weakness and inability to rise in rear without assistance. The Collie could only walk about 10 feet before it would collapse from muscle weakness. The owners were contemplating euthanasia. Physical exam revealed atrophy of hind leg musculature and pain on deep palpitation of hips. Mild proprioceptive deficits in rear were also noted on neurological exam. X-rays revealed moderate DJD of hips but was not deemed severe enough to explain all of the symptoms. A preliminary diagnosis of degenerative myopathy with 2nd degree DJD was made. The Collie was placed on Prednisone for two (2) weeks with mild improvement. On recheck, the Collie was placed on three (3) capsules of the present invention for one month as well as continuation of the Prednisone. At two (2) week recheck, the dog has improved moderately and was able to get up and down on its own. The Prednisone was discontinued and the dog was kept on the capsule of the present invention. At one (1) month recheck, the dog was 50% improved and able to get up and down without assistance and walk around the yard without a wobbly gait. At three (3) months recheck, the dog was significantly improved—walking normally around the yard and going up and down the stairs. The dog is on two (2) capsules two times daily as a maintenance dose. Earlier the dosage was decreased to one (1) capsule two times daily but after one week, the owner noticed an uneasiness in the gait.

Case #4

A 4 year old spayed Dachshund presented with acute yelping in pain when jumping up on a chair. The dog then went off of food and whimpered when picked up. Physical exams revealed pain in lumbar vertebrae. X-rays revealed inter vertebral disk disease at L2–L3 and mild proprioceptive deficits in rear legs 5 were noted. The dog was placed on Prednisone and rest for 2 weeks. At the 2 week check, the dog was clinically normal with mild discomfort on deep palpitation of lumbar vertebrae. The dog was placed on 1 capsule of the present invention, two times daily as a preventative and to strengthen connective tissue of adjacent disk spaces. No further disk disease has taken place.

Case #5

A 1 year old Doberman Pinscher presented with pain on getting up. X-rays were taken and revealed severe dysplasia with osteophyte formation. The dog was placed on three (3) capsules of the present invention, three times daily, for 2 weeks. At 2 week checkup, the dog was in much less pain and is currently doing well on 2 capsules two times daily, maintenance dose.

Case #6

A nine year old cat presented with a limp in the right rear leg. Pain was noticed on extension of the stifle joint.

Radiographs revealed severe DJD in the stifle joint. The cat was placed on one (1) capsule of the present invention, two times daily for one month. At one month recheck, the cat had a mild limp but no pain in the joint. The cat is currently on one (1) capsule four (4) times daily and doing well. The owners reported that they stopped administration of the present invention for one (1) week and the pain returned.

Case #7

A nine year old Doberman Pinscher presented with extreme difficulty rising in the rear, inability to go up and down stairs, and a wobbly gait in the hind quarters. The owners believed the dog to be in constant pain. Myelogram by veterinarian diagnosed cervical vertebral instability with slipped discs at C 5–6, C 6–7. The veterinarian prescribed Prednisone and rest for three weeks and gave prognosis as poor for recovery. The owners said the dog seemed to improve while on Prednisone but symptoms returned when Prednisone was stopped. The dog was placed on three (3) capsules of the present invention, two times daily. At two week recheck, the dog was moving better and getting up easier. At six weeks, the dog was running. At six months, physical exam revealed no pain on manipulation of neck and hips. The dog is currently on three (3) capsules two times daily and doing well.

Case #8

The thoroughbred race horse had a history of chips in ankle. In 1990, the Cornell University Veterinary School worked on the horse. X-rays showed an undiagnosed spot on the ankle. More recent x-rays showed injured sesamoid and joint damage. By 1992, the horse was very lame. The knee was carrying heat and there was little strength in the hock and stifle. The sacroiliac was arthritic and vertebrae slumped so severely that the horse could barely support a rider. The horse rebelled at the track and could not change leads. As a result, the horse was placed on veterinarian list at the track. Use of the powder of the present invention was initiated. The dosage was two (2) scoops two times daily. Within 5 days, the back problem improved to where a rider could be supported and the horse's posture was markedly improved. After 30 days, the horse no longer rebelled upon entering track. The stifle and hock improved in strength and the knee was cold. After 8 weeks, the stifle and hock were tight, and the back was strong. The horse is running two miles without discomfort and will race as soon as track conditions improve. The horse is currently on a maintenance dose of one (1) scoop of the present invention, two times daily increasing to two (2) scoops two times daily during workouts.

Case #9

The thoroughbred race horse was diagnosed with osteoarthritis in the knee and shoulder. The horse was considered lame with very little movement in the shoulder and knee. The knee was carrying heat. Use of the powder of the present invention was initiated at a dosage of three (3) scoops two times daily. After 15 days, the horse showed improved movement in the shoulder. At 25 days, the heat was gone from knee and movement of the horse was markedly improved. The horse is scheduled to begin training approximately six weeks after initiation of treatment with the composition of the present invention.

These cases demonstrate the efficacy of the composition of the present invention. The actions of the animals after treatment is testimony to the improvement in the conditions of the disorder from which the animal suffered prior to treatment with the composition of the present invention. Similar results have been seen with treated humans, but human and animal cases do not need double blind studies. The effect cannot be a placebo, since the animals did not know they were being treated.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A therapeutic composition for treatment and repair of connective tissue in humans and animals comprising: therapeutic quantities of at least one aminosugar selected from the group consisting of glucosamine, glucosamine salts and mixtures thereof, in combination with at least one fragment of a glycosaminoglycan selected from the group consisting of fragments of chondroitin, fragments of chondroitin salts and mixtures of such fragments.

2. The therapeutic composition of claim 1, wherein a dose of the aminosugar ranges from 100 mg to 5,000 mg.

3. The therapeutic composition of claim 2, wherein the dose of the aminosugar for humans and small animals ranges from 100 mg to 2500 mg.

4. The therapeutic composition of claim 2, wherein the dose of the aminosugar for large animals ranges from 500 mg to 5,000 mg.

5. The therapeutic composition of claim 1, wherein a dose of the glycosaminoglycan fragment ranges from 15 mg to 3,000 mg.

6. The therapeutic composition of claim 5, wherein a dose of the glycosaminoglycan fragment for humans and small animals ranges from 15 mg to 500 mg.

7. The therapeutic composition of claim 5, wherein a dose of the glycosaminoglycan fragment for large animals ranges from 100 mg to 3,000 mg.

8. A therapeutic composition for treatment and repair of connective tissue in humans and animals comprising: therapeutic quantities of at least one aminosugar selected from the group consisting of glucosamine, glucosamine salts and mixtures thereof, in combination with at least one fragment of a glycosaminoglycan selected from the group consisting of fragments of chondroitin, fragments of chondroitin salts and mixtures of such fragments, wherein a dose of the aminosugar ranges from 100 mg to 5,000 mg and a dose of the glycosaminoglycan fragment ranges from 15 to 3,000 mg.

9. A method for the treatment and reparation of connective tissue in humans and animals comprising the step of administering therapeutically effective quantities of at least one aminosugar selected from the group consisting of glucosamine, glucosamine salts and mixtures thereof, in combination with at least one fragment of a glycosaminoglycan selected from the group consisting of fragments of chondroitin, fragments of chondroitin salts and mixtures of such fragments, to a human and an animal in need thereof.

10. The method of claim 9, wherein the therapeutic composition is administered orally.

11. The method of claim 9, wherein the therapeutic composition is administered parenterally.

12. A therapeutic composition for treatment and repair of connective tissue in humans and animals, comprising: therapeutic quantities of salts of glucosamine, in combination with chondroitin sulfate fragments for stimulating production of proteoglycans and collagens in humans and animals in need thereof for treatment and repair of the connective tissue.

13. The therapeutic composition of claim 12, wherein the salt of glucosamine is glucosamine hydrochloride.

14. The therapeutic composition of claim 12, wherein the salt of glucosamine is glucosamine sulfate.

15. The therapeutic composition of claim 12, wherein the salt of glucosamine is N-acetylglucosamine.

16. The therapeutic composition of claim 12, wherein a dose of the salt of glucosamine ranges from 100 mg to 5,000 mg.

17. The therapeutic composition of claim 16, wherein the dose of the salt of glucosamine for humans and small animals is approximately 100 mg to 2500 mg.

18. The therapeutic composition of claim 16, wherein the dose of the salt of glucosamine for horses and large animals is approximately 500 mg to 5,000 mg.

19. The therapeutic composition of claim 12, wherein the dose of chondroitin sulfate fragments ranges from 15 mg to 3,000 mg.

20. The therapeutic composition of claim 19, wherein the dose of chondroitin sulfate fragments for humans and small animals is approximately 15 mg to 500 mg.

21. The therapeutic composition of claim 19, wherein the dose of chondroitin sulfate or chondroitin sulfate fragments for horses and large animals is approximately 100 mg to 3,000 mg.

22. The therapeutic composition of any of claims 1–8 or 12–21 further comprising manganese.

23. A method for the treatment and reparation of connective tissue in humans and animals, comprising the step of administering a therapeutically effective quantity of a therapeutic composition including salts of glucosamine in combination with chondroitin sulfate fragments to a human and an animal in need thereof.

* * * * *

UNITED STATES PATENT AND TRADEMARK OFFICE
CERTIFICATE OF CORRECTION

PATENT NO.    : 6,492,349 B1
DATED         : December 10, 2002
INVENTOR(S)   : Robert W. Henderson It is certified that error appears in the above-identified patent and that said Letters Patent is hereby corrected as shown below:

<u>Title page,</u>
Please delete the following:

Related U.S. Application Data

[63] Continuation-in-part of application No. 08/207,581, filed on Mar. 14, 1994, now patent No. 5,587,363, which is a continuation-in-part of application No. 08/040,936, filed on Mar. 31, 1993, now Patent No. 5,364,845."

Signed and Sealed this

Tenth Day of June, 2003

JAMES E. ROGAN
*Director of the United States Patent and Trademark Office*